United States Patent
Ponsati Obiols et al.

(10) Patent No.: US 6,521,599 B2
(45) Date of Patent: Feb. 18, 2003

(54) STABLE PHARMACEUTICAL FORMULATION FOR INTRAVENOUS OR INTRAMUSCULAR ADMINISTRATION OF ACTIVE PEPTIDE COMPOUNDS

(75) Inventors: Berta Ponsati Obiols, Barcelona (ES); Gemma Jodas Farres, Barcelona (ES); Francisco Javier Clemente Rodriguez, Barcelona (ES); Sergi Pavon Fernandez, Barcelona (ES); Jordi Bacardit Cabado, Barcelona (ES)

(73) Assignee: Lipotec, S.A., Barcelona (ES)

( * ) Notice: Subject to any disclaimer, the term of this patent is extended or adjusted under 35 U.S.C. 154(b) by 0 days.

(21) Appl. No.: 09/913,439

(22) PCT Filed: Dec. 15, 2000

(86) PCT No.: PCT/ES00/00476

§ 371 (c)(1),
(2), (4) Date: Oct. 10, 2001

(87) PCT Pub. No.: WO01/43776

PCT Pub. Date: Jun. 21, 2001

(65) Prior Publication Data

US 2002/0128204 A1 Sep. 12, 2002

(30) Foreign Application Priority Data

Dec. 17, 1999 (ES) .............................................. 9902769

(51) Int. Cl.$^7$ .......................... A61K 38/31; A61K 38/12
(52) U.S. Cl. ................ 514/16; 514/11; 514/2; 514/806; 530/311; 530/317; 530/322; 530/329; 930/160; 930/260
(58) Field of Search .......................... 514/11, 9, 2, 806; 530/311, 317, 322, 329; 930/160, 260

(56) References Cited

U.S. PATENT DOCUMENTS 5,753,618 A 5/1998 Harris et al.

FOREIGN PATENT DOCUMENTS

| EP | 0641567 | 3/1995 |
|----|---------|--------|
| ES | 2010561 | 11/1989 |
| WO | 97/47317 | 12/1997 |

Primary Examiner—Karen Cochrane Carlson
Assistant Examiner—B Dell Chism
(74) Attorney, Agent, or Firm—Ostrolenk, Faber, Gerb & Soffen, LLP

(57) ABSTRACT

A stable pharmaceutical formulation for intravenous or intramuscular administration of Octreotide, which is characterized in that the vehicle for injection of the peptide or pharmaceutically acceptable salts thereof contains glycine in concentrations ranging from 10 to 60 mM and aqueous solution of hydrochloric acid in sufficient quantity to adjust the pH of the formulation to values between 3.0 and 4.2.

10 Claims, 2 Drawing Sheets

Figure 1:
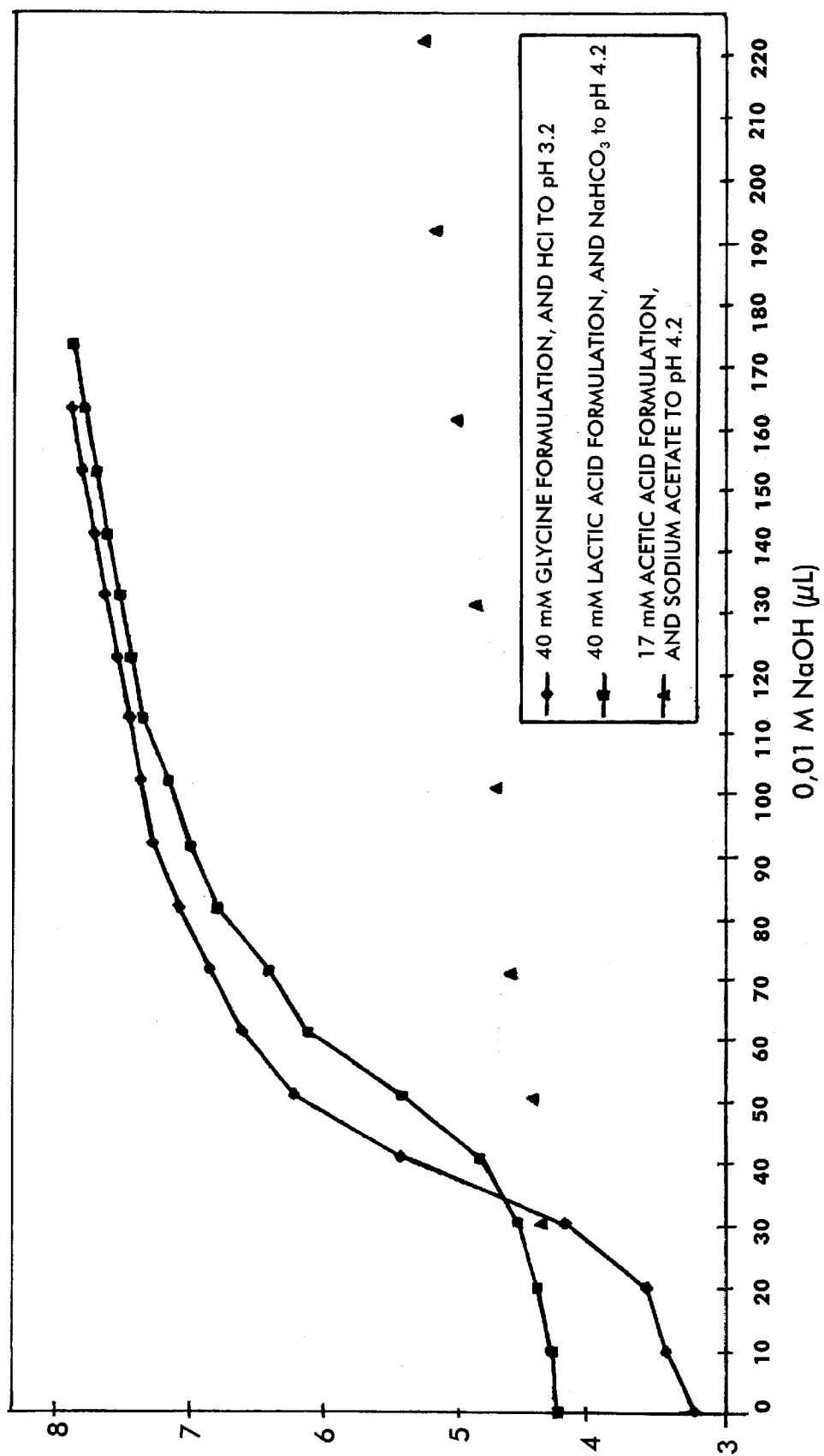

STABLE PHARMACEUTICAL FORMULATION FOR INTRAVENOUS OR INTRAMUSCULAR ADMINISTRATION OF ACTIVE PEPTIDE COMPOUNDS

This invention relates to a stable pharmaceutical formulation, which contains Octreotide as active ingredient for intravenous or intramuscular administration.

As is known, peptides in general, and those that contain a disulphide bridge in particular, present moderate stability in solution. The secondary reactions forming sulphur bridges occur thanks to the presence of free oxygen in the medium. These reactions are favoured by a basic pH. Therefore, to obtain a sufficiently stable formulation the absence of oxygen in the medium and a buffer medium that allows the pH of the solution to be close to 4.0 are required.

From the point of view of compatibility of this system with intravenous administration of the drug, it would be ideal for the pH of the solution to be as near as possible to the physiological pH. This is not possible because, as has been discussed earlier, the formulations at a basic pH do not offer great enough stability. Therefore, for a painless administration of peptides by intravenous route a low strength of the buffer medium in which the active ingredient is dissolved is required so the quantity injected is quickly neutralised by the body of the patient.

From the state of the art, pharmaceutical formulations of peptides that contain acetic acid or lactic acid as vehicle for endogenous administration thereof are already known.

Thus, in the patent ES2010561 (Cavanak, Thomas et al.) a formulation is described that uses a solution of lactic acid and sodium bicarbonate as a vehicle for the intravenous administration of Octreotide.

Furthermore, from the year 1983 to the year 1995, Octreotide was sold dissolved in a solution of acetic acid and sodium acetate as vehicle. However, the formulation that contains acetic acid and sodium acetate presents nociceptive effects and leads to a certain degree of inflammation in the patient.

The nociceptive effect and the production of inflammation are due to the difficulty that the body into which the injection is made has for neutralizing the pH 4.0 solution that is being administered.

The tendency of the current state of the art is to look for administration vehicles which can be neutralized with small quantities of base lacking inflammatory and/or nociceptive effects, and which provide a sufficiently acidic pH, necessary both for aspects relating to production of the product and its storage during its useful life.

The formulation described by Cavanak et al. in the patent above-mentioned follows this tendency as said formulation has a vehicle with lower buffer strength and which, therefore, can be more easily neutralized than the solution with acetic acid and sodium acetate.

A new pharmaceutical formulation has now been discovered for the intravenous or intramuscular administration of Octreotide that contains glycine in addition to the peptide in form of any pharmaceutically acceptable salts thereof and which shows a faster neutralization profile that the existing formulations which contain acetic and lactic acid. Furthermore, injection of the formulation that contains glycine according to the invention is much better tolerated than the formulation with acetic acid and, as with the formulation with lactic acid, lacks nociceptive effects.

Therefore, in accordance with the present invention a novel pharmaceutical formulation is provided which contains Octreotide, or any pharmaceutically acceptable salts thereof, which is characterized in that it contains, as a vehicle for intravenous or intramuscular administration, glycine at concentrations between 10 and 60 mM and because it presents a pH of between 3.0 and 4.2 achieved by means of use of an aqueous solution of hydrochloric acid.

It has been demonstrated that the glycine/HCl formulation of this invention loses buffer strength at pH 3.5 and therefore requires a smaller quantity of base to neutralize it than the formulations with lactic acid/bicarbonate (loss of buffer strength at pH 4.8) and acetic acid/sodium acetate (loss of buffer strength at pH 6.5) belonging to the state of the art.

However, it has been observed that, despite having a lower buffer strength, the formulations with glycine/HCl of this invention offer a high stability between pH 3.0 and 3.6. This fact allows solutions of pH 3.2 to be obtained for intravenous injection in which the Octreotide has a very good stability profile and which is neutralized with small quantites of base.

Furthermore, it has been shown, by means of a study of induction of phlebitis in rabbit ear, using Octreotide as active ingredient, that the effect of injection of the formulation of the present invention dissolved in glycine/HCl in the presence of mannitol as isotonic agent, produces the same effect on the rabbit ears as injection with a control solution of dextrose. The formulation of this invention thus lacks nociceptive and/or inflammatory effects.

As a consequence, the present invention describes the pharmaceutical composition necessary for the application of Octreotide, in form of any pharmaceutically acceptable salts thereof, via intravenous injection. This formulation, which can use different concentrations of glycine and HCl in the range of 10 mM to 60 nM, allows administration, without nociceptive effects or apparent inflammation, of an endovenous injection of Octreotide. This formulation is set to pH values that range from 3.0 to 4.2 and contains an isotonic agent, preferably mannitol or sodium chloride, and optionally an anti-oxidant, preferably phenol.

The invention will now be described with reference to the drawings attached, in which:

FIG. 1 is a graph showing the profiles of neutralization with NaOH of different solutions containing Octreotide as active ingredient:
acetic acid and sodium acetate with sodium chloride as isotonic agent, according to the state of the art.
lactic acid and sodium bicarbonate with mannitol as isotonic agent, according to the state of the art.
glycine and HCl with mannitol as isotonic agent, according to this invention.

Figure 2:
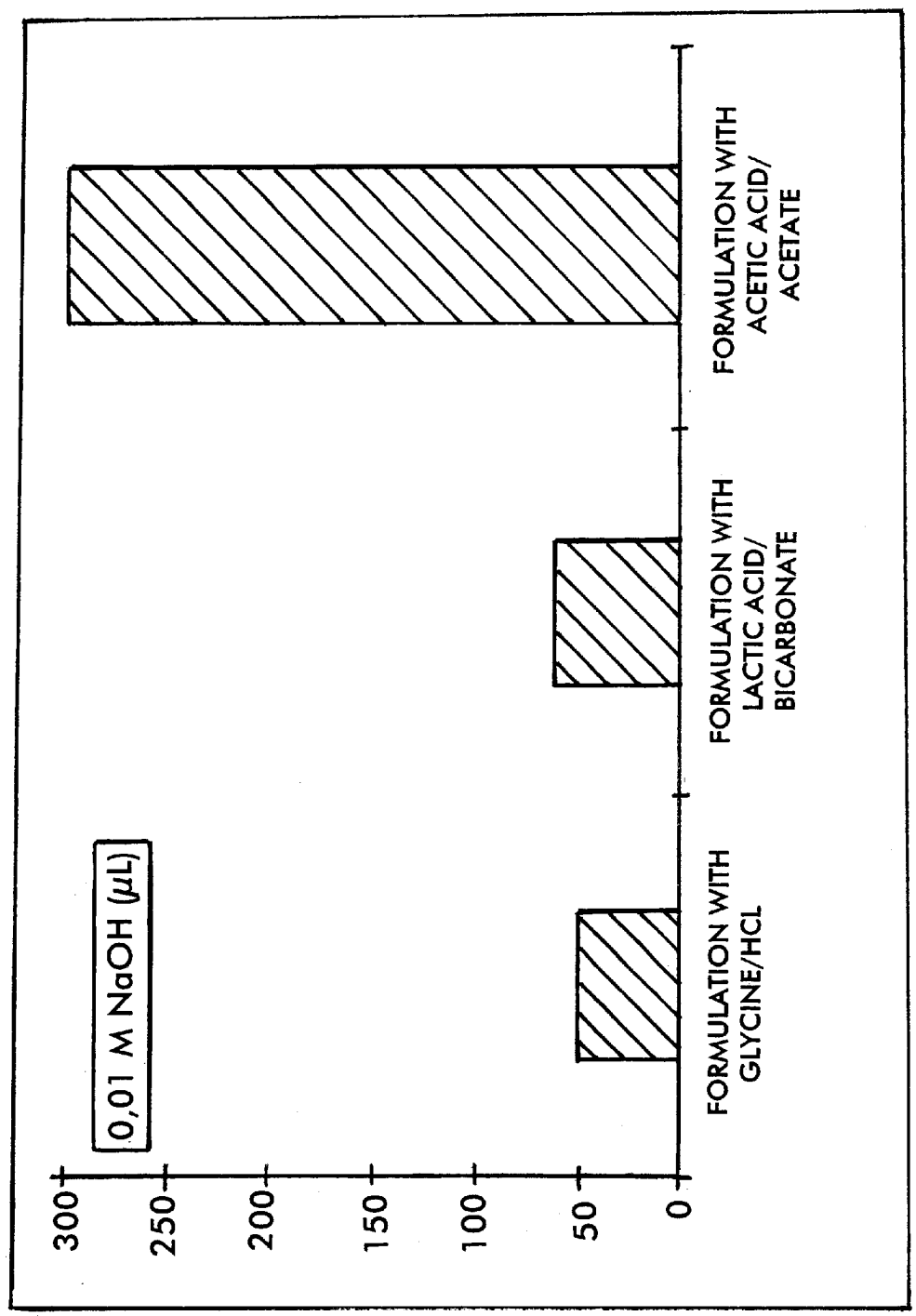

FIG. 2 is a graph showing the quantity of base required to bring each one of the formulations of the state of the art and that of the present invention to physiological pH.

As follows from the graphs of FIGS. 1 and 2, the volume of base required to bring the solution of Octreotide with glycine and hydrochloric acid according to the invention to physiological pH is less than the quantity required for the formulations that contain lactic acid/sodium bicarbonate and acetic acid/sodium acetate of the state of the art.

This fact, as has already been discussed earlier, is important from the point of view of the potential nocicpetive and inflammatory effect of said solutions. The higher the quantity of base that has to be added to bring the solution to physiological pH, the greater the possibility that the solution will produce inflammation and nociceptive effects when administered to the patient by intravenous route.

To corroborate the results obtained in the neutralization curves a study of the induction of phlebitis in rabbits was undertaken when they were injected, by endovenous route in a marginal vein of the ear, with 1 ml of each one of the following solutions:

40 mM glycine and HCl in sufficient quantity to give pH 3.2 with mannitol as isotonic agent, along with 0.1 mg/ml of Octreotide.

20 mM acetic acid and sodium acetate in sufficient quantity to give pH 4.2 with sodium chloride as isotonic agent, along with 0.1 mg/ml of Octreotide.

40 mM lactic acid and sodium bicarbonate in sufficient quantity to give pH 4.2 with mannitol as isotonic agent, along with 0.1 mg/ml of Octreotide.

The result of said studies showed that both the formulation with lactic acid/sodium bicarbonate and the formulation that contained glycine/hydrochloric acid are suitable for intravenous injection of Octreotide, being free both of nociceptive effects and inflammatory effects.

The formulation that contains acetic acid/sodium acetate showed a clear induction of phlebitis in the rabbit ear (edemas up to 9 mm). Furthermore, it also showed a clear nociceptive effect demonstrated by the desire of the rabbits to free themselves from the trap on injecting the sample, an effect that was not observed with the other formulations.

The stability trials of the new formulation of Octreotide with glycine/HCl showed a better behaviour in these terms than the formulation with lactic acid. The formulation with lactic acid presents a greater percentage of related impurities than the formulation with glycine.

Considering that glycine, as an essential amino acid, is present in blood and that there are also a large number of nutritional solutions on the market that are administered by intravenous route and which contain important quantities of amino acids among which glycine can be found, the formulation, object of this invention, which contains glycine/HCl is a good option as an injection vehicle for Octreotide by intravenous route, from the point of view both of product stability and of pain levels in the patient.

The following, non-limiting examples, describe several possible formulations of the invention that include the use of glycine/HCl as administration vehicle for Octreotide.

EXAMPLE 1
(For 1000 Ampoules Containing 0.05 mg of Active Ingredient)

45 grams of apyrogenic mannitol (247 mmoles) are weighed along with 1.5 grams (20 mmoles) of glycine (in accordance with European Pharmacepeia Supplement 2000). 50 mg of Octreotide (free base of acetic acid and water) are added to this mixture. The mixture is dissolved in 900 ml of water for injection and the pH adjusted to 3.2 using an aqueous solution of 0.1 M hydrochloric acid. Once the pH has been set the solution is made up to 1 liter and $CO_2$ bubbled through for a minimum of 10 minutes. Each ampoule is dosed with 1 ml of this solution and then heat sealed. Thus, ampoules are produced containing 0.05 mg of active ingredient in 1 ml of a 20 mM glycine/HCl vehicle with 4.5% mannitol as isotonic agent.

EXAMPLE 2
(For 1000 Ampoules Containing 0.1 mg of Active Ingredient)

45 grams of apyrogenic mannitol (247 mmoles) are weighed along with 1.5 grams (20 mmoles) of glycine (in accordance with European Pharmacepeia Supplement 2000). 100 mg of Octreotide (free base of acetic acid and water) are added to this. The mixture is dissolved in 900 ml of water for injection and the pH adjusted to 3.2 using an aqueous solution of 0.1 M hydrochloric acid. Once the pH has been set the solution is made up to 1 liter and $CO_2$ bubbled through for a minimum of 10 minutes. Each ampoule is dosed with 1 ml of this solution and then heat sealed. Thus, ampoules are produced containing 0.1 mg of active ingredient in 1 ml of a 20 mM glycine/HCl vehicle with 4.5% mannitol as isotonic agent.

EXAMPLE 3
(For 200 Vials Containing 1 mg of Active Ingredient)

45 grams of apyrogenic mannitol (247 mmoles) are weighed along with 1.5 grams (20 mmoles) of glycine (in accordance with European Pharmacepeia Supplement 2000). 200 mg of Octreotide (free base of acetic acid and water) and 1 gram of phenol R are added to this. The mixture is dissolved in 900 ml of water for injection and the pH adjusted to 3.2 using an aqueous solution of 0.1 M hydrochloric acid. Once the pH has been set the solution is made up to 1 liter and $CO_2$ bubbled through for a minimum of 10 minutes. Each vial is dosed with 1 ml of this solution and then sealed with a butyl cap and anti-tampering pre-packaging. Thus, vials are produced containing 1 mg of active ingredient in 5 ml of a 20 mM glycine/HCl vehicle with 4.5% mannitol as isotonic agent with 5 mg of phenol per vial.

What is claimed is:

1. A stable pharmaceutical formulation for intravenous or intramuscular administration of Octreotide, or any pharmaceutically acceptable salt thereof, characterized in that the vehicle for injection of the peptide or pharmaceutically acceptable salts thereof contains glycine in concentrations ranging from 10 to 60 mM and aqueous solution of hydrochloric acid in sufficient quantity to adjust the pH of the formulation to values between 3.0 and 4.2.

2. A pharmaceutical formulation according to claim 1, characterized in that it contains an isotonic agent and, optionally, an anti-oxidant.

3. A pharmaceutical formulation according to claim 1, characterized in that concentration of Octreotide is 0.1 mg/ml.

4. A pharmaceutical formulation according to claim 1, characterized in that concentration of Octreotide is 0.05 mg/ml.

5. A pharmaceutical formulation according to claim 1, characterized in that concentration of Octreotide is 0.2 mg/ml.

6. A pharmaceutical formulation according to claim 1, characterized in that the glycine concentration is preferably 20 mM.

7. A formulation according to claim 1, characterized in that the pH is preferably 3.2.

8. A pharmaceutically acceptable formulation according to claim 2, characterized in that the isotonic agent is preferably sodium chloride.

9. A pharmaceutically acceptable formulation according to claim 2, characterized in that the isotonic agent is preferably mannitol.

10. A pharmaceutically acceptable formulation according to claim 2, characterized in that the anti-oxidant is preferably phenol.

* * * * *